(12) United States Patent
Wang

(10) Patent No.: US 8,036,841 B2
(45) Date of Patent: Oct. 11, 2011

(54) MEASURING METHOD AND APPARATUS FOR POTENTIOMETRIC MEASURING PROBES

(75) Inventor: Changlin Wang, Shanghai (CN)

(73) Assignee: Mettler-Toledo AG, Greifensee (CH)

( * ) Notice: Subject to any disclaimer, the term of this patent is extended or adjusted under 35 U.S.C. 154(b) by 318 days.

(21) Appl. No.: 12/334,008

(22) Filed: Dec. 12, 2008

(65) Prior Publication Data

US 2009/0157338 A1    Jun. 18, 2009

Related U.S. Application Data

(63) Continuation of application No. PCT/EP2007/058947, filed on Aug. 28, 2007.

(30) Foreign Application Priority Data

Aug. 30, 2006   (CN) .......................... 2006 1 0030556

(51) Int. Cl.
  *G01R 35/00*   (2006.01)
(52) U.S. Cl. ............................. 702/65; 702/124; 324/605
(58) Field of Classification Search .................... 702/58, 702/59, 64, 65, 70, 116, 117, 124; 324/602, 324/605, 607, 707, 711
See application file for complete search history.

(56) References Cited

U.S. PATENT DOCUMENTS 4,777,444 A * 10/1988 Beijk et al. .................... 324/439
4,822,456 A *  4/1989 Bryan ........................... 205/789

FOREIGN PATENT DOCUMENTS

| EP | 0 241 601 B1 | 10/1987 |
| EP | 0 497 994 A1 | 8/1992 |
| WO | WO 92/21962 A1 | 12/1992 |
| WO | WO 00/14523 A2 | 3/2000 |

OTHER PUBLICATIONS

Form PCT/ISA/210 (International Search Report dated Nov. 30, 2007.
Comments on the Written Opinion of the International Searching Authority dated Jan. 25, 2008.

* cited by examiner

*Primary Examiner* — Manuel L Barbee
(74) *Attorney, Agent, or Firm* — Buchanan Ingersoll & Rooney PC

(57) ABSTRACT

A method and device are disclosed for measuring potentiometric measuring probes. An exemplary method includes feeding two test voltages comprising a harmonic wave $U_{eg}$ with a base frequency $f_g$ and the harmonic wave $U_{er}$ with a base frequency $f_r$ into two cores of a connecting cable through voltage source impedances, respectively. The voltage between an indicating electrode and a reference electrode, and the AC responding signal resulting from the two test voltages are passed to an amplifier and further to a transfer function unit having transfer functions ($H_g$, $H_r$), an A/D converter, and a Fourier transformation unit, to calculate a potential $U_x$ and the two test responses $U_g$ and $U_r$, respectively. Two calibration responses $U_{ehg}$ and $U_{ehr}$ are determined, wherein $U_{ehg}$ includes a product of $U_{eg}$ and $H_g$, and wherein $U_{ehr}$ includes a product of $U_{er}$ and $H_r$. Functional expressions are established for the test responses $U_g$ and $U_r$, and the internal resistances $R_g$ and $R_r$ are determined by simultaneously solving equations having the unknown resistances $R_g$ and $R_r$ and capacitances $C_1$ and $C2$. Accurate measurement of the internal resistance of the electrode can be achieved even with a relatively long connecting cable.

42 Claims, 7 Drawing Sheets

MEASURING METHOD AND APPARATUS FOR POTENTIOMETRIC MEASURING PROBES

RELATED APPLICATIONS

This application claims priority under 35 U.S.C. §119 to Chinese Application 200610030556.0 filed in China on Aug. 30, 2006, and as a continuation application under 35 U.S.C. §120 to PCT/EP2007/058947 filed as an International Application on Aug. 28, 2007 designating the U.S., the entire contents of which are hereby incorporated by reference in their entireties.

TECHNICAL FIELD

A method and device are disclosed for measuring, monitoring and analyzing the condition of a potentiometric measuring probe with at least two electrodes by measuring the internal resistance of at least one electrode.

BACKGROUND INFORMATION

Potentiometric measuring probes, ionsensitive probes or redox probes, such as pH measuring probes, are used in the electrochemistry. The fundamental structure of such a measuring probe includes two electrochemical half cells, wherein one half cell is referred to as an indicating electrode, for example, a glass electrode with a sensitive membrane, and the other half is referred to as reference electrode or as a reference diaphragm. The potential difference between the two half cells is proportional to the parameter to be measured, such as the pH-value of a solution.

The indicating electrode as well as the reference electrode has a certain internal resistance. As long as the electrodes operate normally, both internal resistances will remain substantially stable. However, in the event of an electrode failure, like the breakage, leakage or malfunction of the electrode membrane or the reference diaphragm the internal resistance of an electrode will change significantly. Consequently, by measuring the internal resistances of the electrodes their condition can be monitored and analyzed.

In order to measure the resistances of the electrodes individually, a third electrode, a so-called solution ground electrode may be inserted into the solution to be measured. Then the internal resistance of the indicating electrode as well as the reference electrode is measured in reference to the solution ground electrode. The resistance of the indicating electrode is very high and can vary over a very large range, whereas the resistance of the reference electrode is usually relatively small but can also vary over a large range.

Further, the potential difference between the electrodes is relatively small and significant capacitances exist between the wires of the connecting cable. All these factors influence the measurements of the internal resistances of the electrodes and have to be taken into account for any measurement or analysis.

To address these problems, numerous measurement methods have been proposed. For example, EP 0 497 994 A1 discloses a method and device for measuring the resistance of the indicating electrode. The disclosed method proposes the use of an alternating test voltage for exciting the connecting cable and the electrode. The signal which relates to the alternating test voltage is separated from the potentiometric measurement signal by a low pass filter and a subtracting unit and is split in the corresponding real and imaginary parts by multiple synchronous rectifiers. However, this method can involve multiple expensive components such as synchronous rectifiers, which can have a significant cost increase, especially in the case of measurement devices with multiple electrodes.

SUMMARY

A method is disclosed for observing (e.g., measuring, monitoring and/or analyzing) the condition of a measuring device having a potentiometric measuring probe which comprises at least two electrodes, each having a resistance, the method comprising: applying an alternating test voltage provided by a voltage source via a connecting cable to at least one of the electrodes; passing a combined signal containing a potentiometric voltage of the electrode and a signal that relates to the applied alternating test voltage to a processing unit; extracting from the combined signal the signal that relates to the applied alternating test voltage in the processing unit; and calculating from the signal that relates to the applied alternating test voltage a resistance of the at least one electrode, wherein the combined signal is processed in the processing unit by a transfer function unit, which substantially simultaneously extracts from the combined signal a measurement value which corresponds to the potentiometric signal of the at least one electrode and a test response that is used for calculating the resistance of the at least one electrode.

A device is disclosed for observing the condition of a potentiometric measuring probe having at least two electrodes, each having an electrical resistance, at least one electrode being connected via a connecting cable to a voltage source configured for providing an alternating test voltage, the device comprising: a processing unit with an input configured to be connected to the connecting cable, and configured to receive a combined signal containing a potentiometric voltage of the at least one electrode and a signal that relates to the applied alternating test voltage and to extract from the combined signal a signal which corresponds to a signal that results from the applied alternating test voltage, wherein the processing unit comprises a transfer function unit configured to substantially simultaneously extract from the combined signal a measurement value which corresponds to the potentiometric voltage of the at least one electrode which is provided at a first output, and a test response which is provided via a second output to a calculation unit.

BRIEF DESCRIPTION OF THE DRAWINGS

Features and advantages of the present disclosure will now be described with reference to the accompanying drawings and specific embodiments, wherein.

DETAILED DESCRIPTION

Figure 1:
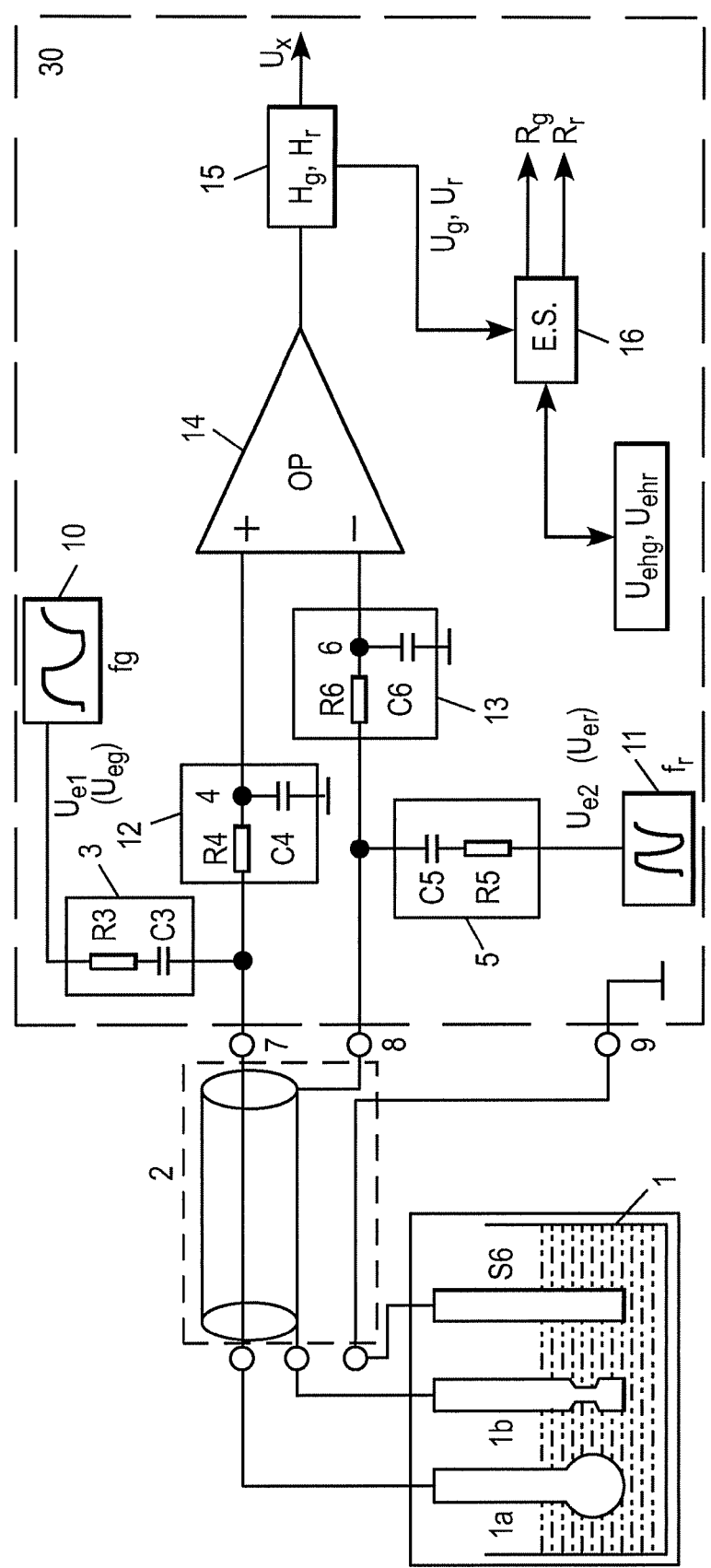
FIG. 1 is a schematic view of an exemplary structure of a measuring device for a potentiometric measuring probe according to an embodiment of the disclosure, together with an electrode and a connecting cable.

A measuring method and device are disclosed for potentiometric measuring probes that can provide accurate and cost effective measurements of the potential difference of probe electrodes as well as of the resistance of a potentiometric electrode, in particular the resistances of an indicating electrode and/or a reference electrode.

An exemplary method is disclosed for observing (e.g., measuring, monitoring and/or analyzing) the condition of a potentiometric measuring probe which comprises at least two electrodes, each having a resistance, and comprises:

applying an alternating test voltage provided by a voltage source via a connecting cable to at least one of the electrodes;

passing a combined signal consisting of the potentiometric voltage of the at least one electrode and a signal that relates to the applied alternating test voltage to a processing unit;

extracting from the combined signal the signal that results from the applied alternating test voltage in the processing unit; and calculating from the signal that relates to the applied alternating test voltage (Ue1, Ue2) the resistance of the electrode.

The combined signal can be processed in the processing unit by a transfer function unit, which substantially simultaneously extracts from the combined signal a measurement value which corresponds to the potentiometric signal of the at least one electrode and a test response that is used for calculating the resistance of the electrode. An exemplary method and corresponding device can provide an advantage in that the test response, which relates to the applied alternating test voltage, can be extracted from the combined signal by means of a simple and cost effective device.

In addition, exemplary methods according to the disclosure can be highly accurate, because the impact of different components and their coupling can be included in the transfer function. For example because of the structure of the connecting cable, a certain degree of coupling exists between the resistances and capacitances of the electrodes which result as mutual influence. This mutual influence is maintained during the extraction by means of the transfer function unit and is available for the determination of the resistance of the electrode.

Further, by the substantially simultaneous extraction of the test response, the measurement values of the potentiometric voltage and a signal that results from the applied alternating test voltage can be compared and/or correlated immediately in the calculation unit.

In a further exemplary embodiment of the disclosure, the alternating test voltage is, where appropriate after the subtraction of a constant voltage component, substantially symmetrical in relation to their negative and positive voltage values. For example, the alternating test voltage comprises a sine shaped signal component with a base frequency, in particular during the whole time or during a calibration time period and can comprise at least one further sine shaped, harmonic signal component corresponding to the base frequency, in particular during the whole time, or during a testing time period during which the alternating test voltage is applied to the at least one electrode.

According to a further embodiment, a least two alternating test voltages can be applied, each comprising a set of at least one signal component corresponding to the base frequency wherein the sets between each of the alternating test voltages are disjunctive. Further, the base frequencies ($f_g$, $f_r$) of the alternating test voltages can differ by the ratio (m) according to the expression: $f_g=m*f_r$ or $f_r=m*f_g$, wherein $f_g$ is the first base frequency and $f_r$ is the second base frequency and m is an even number larger than or equal to 2. The measuring probe can comprise two electrodes, with a first alternating test voltage applied to the first electrode and a second alternating test voltages applied to the second electrode. These forms of the alternating test voltage can have the advantage that they can be separated easily from the each other and from the potentiometric signal.

In an exemplary configuration, the first and the second alternating test voltages simultaneously met the following conditions as described above: the first alternating test voltage is substantially symmetrical and the second base frequency is an even numbered multiple of the first base frequency. This results in the situation that no component of the second base frequency is included in the first alternating test voltage and no component of the first base frequency is included in the second alternating test voltages.

In a further exemplary embodiment of the disclosure, the combined signal is processed by calculating at least one frequency component of a Fourier Transformation, which can be based on a Fast Fourier Transformation (FFT) algorithm, and the test response can be extracted corresponding to at least one base frequency component of the alternating test voltage. The frequency component calculation can be configured to determine only those components of the frequency spectrum which are required for the calculation of output signals. For example, only the constant component and the first order component of the alternating test voltage and/or a calibration voltage is calculated.

In an exemplary embodiment of the disclosure, the combined signal is analog-digital converted and passed, where appropriate after digital low pass filtering, to the Fourier transformation unit or to a calculation unit. Further, the combined signal can be preprocessed and/or amplified and/or converted by one or multiple amplifiers and passed, where appropriate via a low pass filter, to the input of an A/D converter or to a Fourier transformation unit or to a calculation unit.

All these processing steps can be implemented in a transfer function unit, which can comprise an operational amplifier, an A/D converter and a Fourier transformation unit, which are connected in series. The transfer function unit may further comprise filter means, which comprises a low pass filter or a low pass filter and a digital filter, wherein the low pass filter is connected between the input of the transfer function unit and the A/D converter and the digital filter is connected between the A/D converter and the Fourier Transformation unit.

In a further embodiment of the disclosure, a method comprises a calibration process for determining at least one calibration response during a calibration process, in particular by applying an alternating sine voltage to the at least one electrode.

In an exemplary embodiment during a calibration process, the at least one calibration response is determined by replacing the resistance of the at least one electrode by a calibration resistance. The calibration response can be determined by a 4-point-calibration which is conduced by selecting four different settings of a pair of calibration resistances ($R_g$, $R_r$), the first value of the pair representing the resistance of the first electrode (1a) and the second value representing the resistance of the second electrode (1b), or by a 2-point-calibration process by selecting two different calibration resistances ($R_{g0}$ and $R_{g1}$) for the first electrode (1a). In particular, in the four-point-calibration the four calibration points are chosen to be ($R_{g0}$, 0), ($R_{g1}$, 0), (0, $R_{r0}$) and (0, $R_{r1}$), with $R_{g0}$ and $R_{g1}$ as well as $R_{r0}$ and $R_{r1}$ being different calibration resistances.

In a further embodiment of the disclosure, during the calibration process at least one response coefficient is calculated from an impedance equation, which comprises at least one impedance of the measuring device. The response coefficient reflects the known circuit structure and can be stored as an intermediate value and used for the recurring measurements. This way the calculation effort for the potentiometric measurements can largely be reduced.

In an exemplary embodiment of the disclosure, the resistance of the electrode is determined by solving an impedance equation, which corresponds to the measuring device and which relates the test response to the resistance of the at least one electrode. A first impedance equation for a first test response and a second impedance equation for a second test response can be solved simultaneously to determine a first resistance and a second resistance. By solving the impedance equation corresponding to the measuring device, the effects of the impedances, in particular the coupling between the resistances and the capacitances are taken into account to improve the accuracy of the measurements especially for long connecting cables.

The impedance equation of the measuring device may comprise the impedance of the electrode and/or the impedance of the connecting cable and/or the impedance of the processing unit and/or a DC-blocking/current-limiting impedance of the voltage source and/or an impedance of a filtering unit that filters the combined signal received at the input of the processing unit. Further, the impedance equation can be advantageously solved by including at least one (e.g., previously determined) intermediate value, which in particular is given by at least one calibration response and/or by at least one response coefficient. In this embodiment, the impedance equation can take into account many different forms of impedances and does not require that the non-phase-shifting or base frequency-independent part of the total impedance be formed by the resistance of the electrode only. Therefore, the method is suitable for relative complex input circuits rather then being limited to strong simplification, like connecting a pure capacitance in series to the resistance of the electrode which results in an inaccurate high-pass characteristic. The present embodiment of the disclosure can account for numerous input impedances and therefore improve the accuracy of the measurements.

In a further exemplary embodiment, the measuring device comprises an amplifier, which is connected with its input via the connecting cable to the at least one electrode and with its output to the transfer function unit and which preprocesses (e.g., amplifies and/or converts) the combined signal. A first electrode can be connected to a first input of the amplifier and a second electrode is connected to a second input of the amplifier, which provides on its output a combined signal which corresponds to the difference of the combined signal of a first electrode and the combined signal of the second electrode.

Further, in an exemplary embodiment of the disclosure the voltage source comprises a DC-blocking and/or current-limiting impedance which, for example, comprises a capacitor and/or a resistor, wherein the electrode is connected to the voltage source via said DC-blocking and/or current-limiting impedance.

In a further embodiment of the disclosure, the electrode is connected via a filtering unit, which can be a RC low pass filter circuit comprising a capacitor and a resistor, to the transfer function unit or to an amplifier. This way a relatively simple input circuit with a filtering unit can be included in the determination of the impedance equation and the resistance of the electrode and consequently the accuracy of the measurement can be improved.

For example this can be applied when the circuit of the measuring system comprises components such as commonly used resistors and capacitors for anti-EMC and anti-ESD. Even in the case that these components contribute to a rather complex impedance characteristic of the overall system their influence of these components is accounted for in the determination of the resistance of the electrode.

FIG. 1 represents a schematic structural view of an electrode, a connecting cable and a measuring device for a potentiometric measuring probe according to an embodiment of the present disclosure. The device is used to measure the electrode potential $U_x$, and the internal resistances $R_g$ and $R_r$. The probe is positioned in the solution to be measured and the probe 1 comprises an indicating electrode 1a, a reference electrode 1b and a solution ground electrode SG, wherein the indicating electrode 1a and the reference electrode 1b are connected to the measuring device 30 via two different cores of the connecting cable 2, while the solution grounding electrode SG is grounded. The indicating electrode 1a can be connected via a center core of the connecting cable 2, the reference electrode 1b can be connected via a first shield surrounding the center core of the connecting cable 2, and the solution ground electrode SG can be connected via a second shield surrounding the first shield. The indicating electrode 1a has an internal resistance $R_g$, and the reference electrode 1b has an internal resistance $R_r$. The electrode 1 and the connecting cable 2 with their electrical function correspond to the equivalent circuit diagram of FIG. 2.

Figure 2:
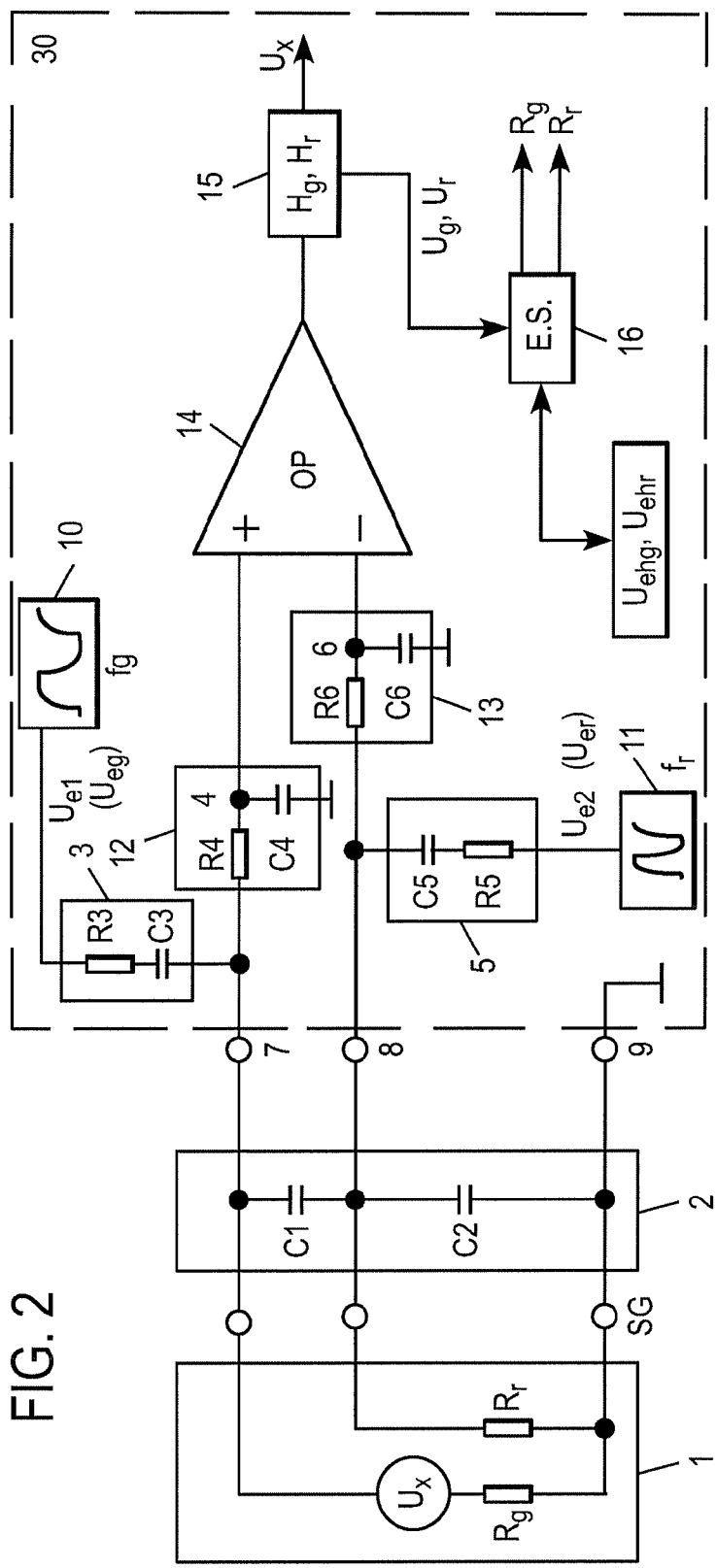
FIG. 2 is an equivalent circuit diagram of FIG. 1.

FIG. 2 represents the equivalent circuit diagram of FIG. 1. As shown in FIG. 2, the probe 1 is represented as a voltage source having an electrode potential $U_x$ and two electrode resistors $R_g$, $R_r$ connected in series whereby the junction between $R_g$ and $R_r$ is grounded via the solution ground electrode SG. In accordance with the structure of the commonly used connecting cable, the connecting cable 2 is represented as capacitors $C_1$ and $C_2$. The capacitor $C_1$ is connected in parallel to the probe between the connecting points 7 and 8. For other connecting cables, the circuit and its way of connection may slightly vary leading to slight variations in the expressions and equations presented here, nevertheless, the principles and methodologies are the same.

Referring now to FIG. 2, the measuring device 30 comprises a first voltage source 10, a second voltage source 11, first voltage source impedance 3, second voltage source impedance 5, a transfer function unit 15 and a calculation unit 16.

The first voltage source 10 generates a first test voltage $U_{e1}$, which includes a harmonic wave $U_{eg}$ with a basic wave base frequency $f_g$. The second voltage source 11 generates a second test voltage $U_{e2}$, which comprises a harmonic wave $U_{er}$ with a basic wave base frequency $f_r$. In order to avoid mutual interference thereof during the Fourier transformation procedures, the frequencies fr and fg are chosen to have disjunctive base frequency components. This means that no harmonic wave component of the base frequency fr is present in the spectrum of the exciting voltage Ue1, and no harmonic wave component of the base frequency fg is present in the spectrum of the exciting voltage Ue2. This can be achieved by using a first test voltage having a waveform with strictly symmetric positive and negative halves (e.g. the use of the square shaped function, and the like). In that way, the waveform can only comprise harmonic waves with frequencies of $3f_g$, $5f_g$, etc. and not even order harmonic waves, such as $2f_g$, $4f_g$, etc. At the same time let fr=m*fg, m being an even number equal to or larger than 2.

The first voltage source impedance 3 is connected between an output of said first voltage source 10 and one of the cores of the connecting cable, such as to the connection point 7, applying the test voltage $U_{e1}$ thereon. The second voltage source impedance 5 is connected between an output of said second voltage source 11 and the other core of the connecting cable, such as to the connection point 8, applying the test voltage $U_{e2}$ thereon. The first voltage source impedance 3 and the second voltage source impedance 5 can solely comprise capacitors. However, in this embodiment a resistor $R_3$ and a capacitor $C_3$, are connected in series to constitute the first voltage source impedance 3. Similar, a resistor $R_5$ and a capacitor $C_5$, are connected in series to constitute the second voltage source impedance 5. For cost effectiveness considerations, resistors $R_3$ and $R_5$ are used for current limitation, because a resistor is usually much cheaper than a capacitor with similar accuracy and temperature coefficient. In addition, with the use of a resistor high base frequency harmonic waves will not increase. Further, the capacitors $C_3$ and $C_5$ function to block the direct current from the voltage generating unit 10.

Between the connection points 7 and 8 and the two inputs of a differential amplifier 14, there can be filtering units 12 and 13, to reduce electromagnetic interference and electrostatic shock. Each filtering unit 12 and 13 comprises a RC low pass filter circuit, for example comprising a resistor $R_4$ and a capacitor $C_4$, and respectively a resistor $R_6$ and a capacitor $C_6$. In addition to resistive and capacitive elements, inductive elements can also be included in the filtering units 12 and 13, for example ferrites. However, since the test voltage $U_{e1}$ or $U_{e2}$ for measuring the resistances $R_g$ and $R_r$ can have low frequencies, the inductive elements can be neglected for the determination of $R_g$ and $R_r$, Consequently, inductive elements are not mentioned in the equations described below. Nevertheless, the present method and device can also be used with inductive elements.

The output of the filtering unit 12 is provided at the connecting point 4, which is connected to the non-inverting input of the differential amplifier 14, whereas the output of the filtering unit 13 is provided at the connecting point 6, which is connected to the inverting input of the differential amplifier 14.

Figure 3:
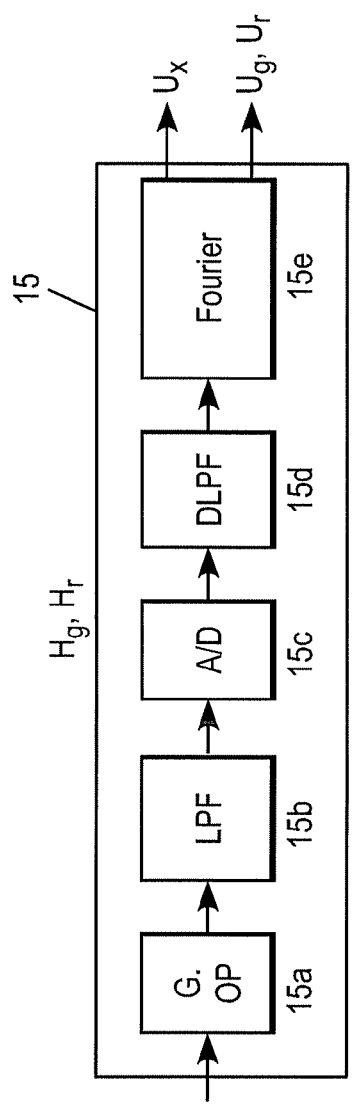
FIG. 3 is an exemplary structural block diagram of the transfer function unit of FIG. 2.

Referring now to FIG. 3, the transfer function unit 15 comprises an A/D converter 15c and Fourier transformation unit 15e. The transfer function unit 15 can also comprise one or multiple operational amplifiers 15a preceding the A/D converter 15c. The Fourier transformation unit 15e is used to calculate the potential $U_x$ of the potentiometric measuring probe and two test responses $U_g$ and $U_r$. A low pass filter 15b can also be inserted preceding the A/D converter to reduce the possible aliasing errors of the A/D sampling. The output values X(i) of the A/D converter 15c are the digital values corresponding to the input signal. If required, a digital low-pass filter 15d can be included following the A/D conversion to carry out digital filtering to further eliminate high base frequency interferences. The total transfer function of the modules in the transfer function unit 15 can be represented by $H_g$ and $H_r$, $H_g$ representing the general transfer function for the signal with the base frequency $f_g$ and $H_r$ representing the general transfer function for the signal with the base frequency $f_r$.

The operational amplifier 15a can also include the transfer function, in particular the gain of the amplifier 14. Thus, the transfer functions $H_g$, $H_r$ can also include the transfer functions of the amplifier 14.

Referring again to FIG. 2, the test responses $U_g$ and $U_r$ can be obtained from measurements as well as calculation. The sine voltage $U_{eg}$ with $f_g$, the sine voltage $U_{er}$ with $f_r$ and the transfer functions $H_g$, $H_r$ are known. From all the circuit elements only the resistances Rg, and Rr and the capacitances C1 and C2 are unknown. Therefore, by simultaneously solving the equations for the test responses Ug, and Ur, the equations for the resistances Rg, Rr, capacitances C1, C2 are established, and the resistances Rg and Rr can be calculated.

The calculation unit 16, which connected to the output terminal of the Fourier transformation unit 15e of the transfer function unit 15, can derive the internal resistance $R_g$ of the indicating electrode and the internal resistance $R_r$ of the reference electrode based on the known test responses $U_g$ and $U_r$ and the known structure and parameters of the circuit through the complex simultaneous equations for $R_g$, $R_r$, $C_1$ and $C_2$.

However, it can be intricate to determine the signal transfer functions Hg and Hr from the amplifier 14, the low pass filter 15b, the A/D converter 15c, the digital filter 15d and the Fourier transformation unit 15e. The accurate determination of the sine voltage $U_{eg}$ and $U_{er}$ from the test voltages $U_{e1}$ and $U_{e2}$ can also be a complex task. However, all these complex expressions can be solved as a whole by using 4-point-calibration for the determination of two calibration responses $U_{ehg}$ and $U_{ehr}$, wherein $U_{ehg}=U_{eg}*H_g$, and $U_{ehr}=U_{er}*H_r$. The calibration responses $U_{ehg}$ and $U_{ehr}$ or their equivalent parameters are stored in a memory for further use. The 4 calibration points can be (Rg, Rr)=(Rg0, 0), (Rg1, 0), (0, Rr1), (0, Rr2).

In an exemplary embodiment, the transfer function $H_g$ stays either the same throughout the measurement and the calibration or its difference is known. The amplitude, waveform, and phase of the first test voltage $U_{e1}$ stay the same throughout the measurement and the calibration, or their differences are known. Alternatively the sine voltage $U_{eg}$ with $f_g$ stays the same throughout the measurement and the calibration or its difference is known. Similarly, the transfer function $H_r$ stays the same during the measurement and the calibration or their difference is known. The amplitude, waveform, and phase of the second test voltage $U_{e2}$ stays the same during the measurement and the calibration or its difference are known. Alternatively, the sine voltage $U_{er}$ with $f_r$ stays the same during the measurement and the calibration or their difference is known. In this way, the internal resistances $R_g$ and $R_r$ can be determined by solving the simultaneous equations as described above.

Figure 4:
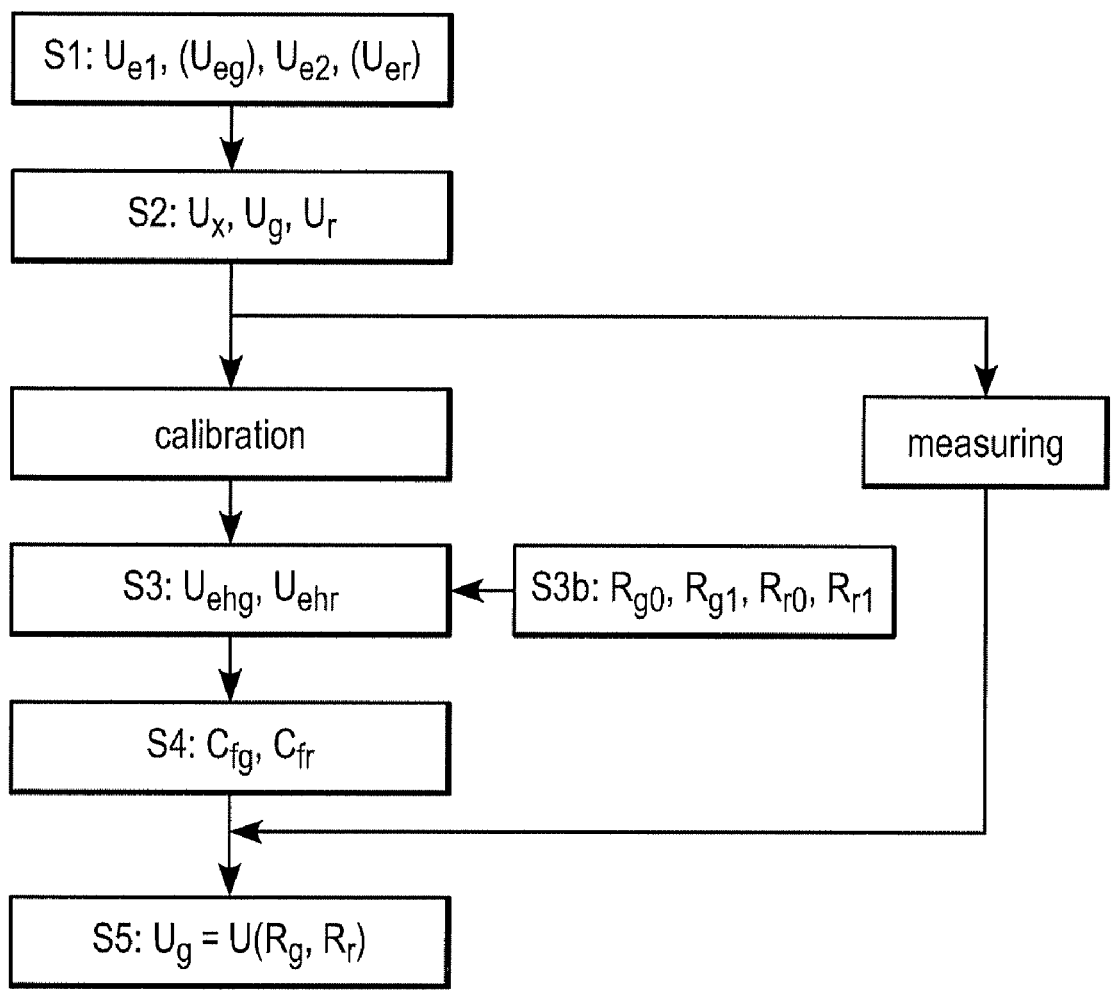
FIG. 4 is a corresponding exemplary flowchart of a measuring method for the measuring device according to the diagram of FIG. 2.

Referring now to FIG. 4, a corresponding flowchart of the measuring method for the measuring device according to the equivalent circuit diagram of FIG. 2 comprising the following exemplary steps:

In step S1 two test voltages $U_{e1}$ and $U_{e2}$ are applied to the two cores of the connecting cable, namely to the connecting points 7 and 8, through the voltage source impedances 3 and 5, respectively. The test voltage $U_{e1}$ comprises the harmonic wave $U_{eg}$ with a base frequency $f_g$, while the test voltage $U_{e2}$ comprises the harmonic wave $U_{er}$ with a base frequency $f_r$. Neither the base frequency $f_r$ of the first test voltage $U_{e1}$ nor the base frequency $f_g$ of the second test voltage $U_{e2}$ have a harmonic wave component in common. This can be achieved if the form of the signal of the first test voltage $U_{e1}$ has strictly symmetric positive and negative halves (e.g. the use of the square wave, and the like). That means that the waveform can only have uneven harmonic waves of $3f_g$, $5f_g$, etc., and even harmonic waves, such as $2f_g$, $4f_g$, etc. do not exist. In that case, $f_r$ can be expressed as $f_r = m*f_g$, with m being an even number equal to or larger than 2.

In step S2: the AC responding signal $U_g$ resulting of the indicating electrode 1a and the AC responding signal $U_r$ resulting of the reference electrode 1b, are passed through a differential amplifier 14, an A/D converter 15c and a Fourier transformation unit 15e, to determine the potential $U_x$ of the potentiometric measuring probe and two test responses $U_g$ and $U_r$. The calculation is presented in more detail below:

The A/D converted signal is passed through the digital filter to get the voltage sequence: U(i) with $i=0, 1, 2 \ldots, n*M-1$, with n and M defined below.

Let the time period of sampling cycle be T with M*T being equal to the time period of at cycle of the excitation base frequency $f_g$ and with M being a natural number.

Next, let $fr = m*fg$ with M*T/m being equal to the time period of one cycle of the excitation base frequency fr with M/m being a natural number; and further let n*M be a common multiple of M and M/m.

A Fourier transformation can be implemented as:

$$U_x = \frac{1}{nM} \sum_{i=0}^{nM-1} U(i)$$

$$U_g = \frac{2}{nM} \sum_{i=0}^{nM-1} U(i)\cos\left(\frac{i}{M}2\pi\right) - \frac{2j}{nM} \sum_{i=0}^{nM-1} U(i)\sin\left(\frac{i}{M}2\pi\right)$$

$$U_r = \frac{2}{nM} \sum_{i=0}^{nM-1} U(i)\cos\left(\frac{i}{M}2m\pi\right) - \frac{2j}{nM} \sum_{i=0}^{nM-1} U(i)\sin\left(\frac{i}{M}2m\pi\right)$$

If $f_r = 2 * f_g$, $$U_r = \frac{2}{nM} \sum_{i=0}^{nM-1} U(i)\cos\left(\frac{i}{M}4\pi\right) - \frac{2j}{nM} \sum_{i=0}^{nM-1} U(i)\sin\left(\frac{i}{M}4\pi\right)$$

The number of multiplications in the calculation above can be reduced by using a method similar to the fast Fourier transformation, if the number M is selected properly. The calculation of the test response $U_r$ will not be disturbed by $U_{e1}$ or $U_{eg}$, as there is no even-order harmonic wave component, such as 2fg, 4fg, in the test voltage $U_{e1}$.

In step S3 two calibration responses $U_{ehg}$ and $U_{ehr}$ are predetermined, wherein $U_{ehg}$ comprises the product of the sine voltage $U_{eg}$ with the transfer function $H_g$, and $U_{ehr}$ comprises the product of the sine voltage $U_{er}$ with the transfer function $H_r$.

The calibration responses $U_{ehg}$ and $U_{ehr}$ may further comprise other definite product factors. $U_{ehg}$ and $U_{ehr}$ comprising other definite product factors are considered as the equivalent parameters of $U_{ehg}$ and $U_{ehr}$. Hg is the transfer function of a signal with base frequency fg, which is fed into the differential amplifier 14, passed, if applicable through the low pass filter 15b, through the A/D converter 15c, if applicable through the digital low pass filter 15d, to the Fourier transformation unit 15e. Similarly, Hr is the transfer function of a signal with the base frequency $f_r$, which is fed into the differential amplifier 14, passed, if applicable through the low pass filter 15b, through the A/D converter 15c, if applicable through the digital low pass filter 15d, to the Fourier transformation unit 15e. The calibration responses $U_{ehg}$ and $U_{ehr}$ can then be determined by a 4-point-calibration, which will be described in further detail below in step S3a.

In step S4, based on the structural parameters of the circuit, functional expressions for the test responses $U_g$ and $U_r$ are established, wherein the test response $U_g$ comprises the product of the calibration response $U_{ehg}$ and a first response coefficient $C_{fg}$ defined by the structure and parameters of the circuit, and the test response $U_r$ comprises the product of the calibration response $U_{ehr}$ and a second response coefficient $C_{fr}$ defined by the structure and parameters of the circuit. They can be specifically derived as follows:

For the base frequency $f_g$:

$$X_{Ckg} = -\frac{1}{2\pi \cdot f_g C_k}, \quad \text{with } k = 1, 2 \ldots 6$$

$$Z_{Ckg} = jX_{Ckg}, \quad \text{with } k = 1, 2 \ldots 6$$

$$Z_{kg} = R_k + Z_{Ckg}, \quad \text{with } k = 3, 4, 5, 6$$

wherein the parameters corresponding to $k=3, 4, 5$ and 6 are known parameters.

$$H_{4g} = \frac{Z_{C4g}}{Z_{4g}}$$

$$Z_{8g} = \left(\frac{1}{R_r} + \frac{1}{Z_{C2g}} + \frac{1}{Z_{5g}} + \frac{1}{Z_{6g}}\right)^{-1}$$

$$Z_{7g} = \left(\frac{1}{Z_{8g} + Z_{C1g}} + \frac{1}{R_g} + \frac{1}{Z_{4g}}\right)^{-1}$$

The voltage of the nodes 4 and 6, relating to the base frequency $f_g$, can be derived according to the expression:

$$U_{4g} = U_{eg} \frac{Z_{7g}}{Z_{7g} + Z_{3g}} \cdot \frac{Z_{C4g}}{Z_{4g}}$$

$$U_{6g} = U_{eg} \frac{Z_{7g}}{Z_{7g} + Z_{3g}} \cdot \frac{Z_{8g}}{Z_{8g} + Z_{C1g}} \cdot \frac{Z_{C6g}}{Z_{6g}}$$

The relation between the input of operational amplification and the output of Fourier transformation is:

$$U_g = (U_{4g} - U_{6g})H_g$$
$$= U_{eg} \frac{Z_{7g}}{Z_{7g} + Z_{3g}} H_{4g}\left(1 - \frac{Z_{8g}}{Z_{8g} + Z_{C1g}}A\right)H_g$$

with $$A = \frac{Z_{C6g}}{Z_{6g}} \cdot \frac{Z_{4g}}{Z_{C4g}}.$$

Let the calibration response $U_{ehg}$ be $$U_{ehg} = U_{eg} \cdot H_g$$

and $$\frac{U_g}{U_{ehg}} = \frac{Z_{7g}}{Z_{7g} + Z_{3g}} H_{4g}\left(1 - \frac{Z_{8g}}{Z_{8g} + Z_{C1g}}A\right)$$

The first response coefficient $C_{fg}$ is the term on the right hand side of the equals sign. In order to avoid the calculation of $H_{4g}$ in the real-time calculation, $U_{ehg}$ may be defined as $U_{ehg} = U_{eg} \cdot H_g \cdot H_{4g}$. This would be equivalent to the previous definition of the calibration response.

For the base frequency $f_r$:

$$X_{Ckr} = -\frac{1}{2\pi \cdot f_r C_k}, \quad \text{with } k = 1, 2 \ldots 6,$$

$$Z_{Ckg} = jX_{Ckr}, \quad \text{with } k = 1, 2 \ldots 6,$$

$$Z_{kr} = R_k + Z_{Ckr}, \quad \text{with } k = 3, 4, 5, 6,$$

wherein the parameters corresponding to k=3, 4, 5, 6 are known parameters.

$$H_{6r} = \frac{Z_{C6r}}{Z_{6r}}$$

$$Z_{7r} = \left(\frac{1}{R_g} + \frac{1}{Z_{3r}} + \frac{1}{Z_{4r}}\right)^{-1}$$

$$Z_{8r} = \left(\frac{1}{Z_{7r} + Z_{C1r}} + \frac{1}{R_r} + \frac{1}{Z_{C2r}} + \frac{1}{Z_{6r}}\right)^{-1}$$

The voltage of the nodes 4 and 6, relating to the base frequency $f_r$, can be derived according to the expression:

$$U_{6r} = U_{er} \frac{Z_{8r}}{Z_{8r} + Z_{5r}} * \frac{Z_{C6r}}{Z_{6r}}$$

$$U_{4r} = U_{er} \frac{Z_{8r}}{Z_{8r} + Z_{5r}} \cdot \frac{Z_{7r}}{Z_{7r} + Z_{C1r}} \cdot \frac{Z_{C4r}}{Z_{4r}}$$

The relation between the input of operational amplification and the output of Fourier transformation is:

$$U_r = (U_{4r} - U_{6r})H_r =$$

$$-U_{er}\frac{Z_{8r}}{Z_{8r}+Z_{5r}}H_{6r}\left(1 - \frac{Z_{7r}}{Z_{7r}+Z_{C1r}}B\right)H_r \text{ wherein } B = \frac{Z_{C4r}}{Z_{4r}} * \frac{Z_{6r}}{Z_{C6r}}.$$

Let the calibration response be $U_{ehr}=-U_{er}*H_r$, then $$\frac{U_r}{U_{ehr}} = \frac{Z_{8r}}{Z_{8r}+Z_{5r}}H_{6r}\left(1 - \frac{Z_{7r}}{Z_{7r}+Z_{C1r}}B\right),$$

wherein the term on the right hand side of the equals sign is the second response coefficient $C_{fr}$.

In step S5 the impedance equations are simultaneously solved:

$$\frac{U_{ehg}}{U_g} = \left(1 + \frac{Z_{3g}}{Z_{7g}}\right)\frac{1}{H_{4g}}\left(\frac{Z_{C1g}+Z_{8g}}{Z_{C1g}+(1-A)Z_{8g}}\right)$$

$$\frac{U_{ehr}}{U_r} = \left(1 + \frac{Z_{5r}}{Z_{8r}}\right)\cdot\frac{1}{H_{6r}}\left(\frac{Z_{C1r}+Z_{7r}}{Z_{C1r}+(1-B)Z_{7r}}\right)$$

wherein the AC responding complex voltage $U_g$ and $U_r$ may be determined by the Fourier transformation.

As the values on the left side of the equal signs of the equations described above are known, there are a total of four unknown parameters, which are resistances $R_g$, $R_r$ and capacitances $C_1$, $C_2$. Resistances $R_g$, $R_r$ and capacitances $C_1$, $C_2$ can be derived by various mathematical or numerical methods, wherein $R_g$ and $R_r$ are the resistances to be measured.

The known two AC responding complex voltages $U_g$ and $U_r$, together with the two calibration responses $U_{ehg}$ and $U_{ehr}$, are fed into a calculation unit 16 capable to process complex numbers, where the internal resistance $R_g$ of the indicating electrode 1a and the internal resistance $R_r$ of the reference electrode 1b are determined based on the functional expressions for the first response coefficient $C_{fg}$ and the second response coefficient $C_{fr}$ by simultaneously solving the equations comprising the unknown resistances $R_g$ and $R_r$ and the unknown capacitances $C_1$ and $C_2$.

A solution procedure is described below:

For the purpose of simplicity, let the resistances be $R_3=R_4$, the capacitances be $C_4=C_6$, that is, A=1, B=1, although this assumption is not necessary. Further, as the influence of the resistance $R_r$ and capacitance $C_2$ on $U_g$ is relatively small, iteration can be a very effective way to solve the abovementioned equations.

The basic equations relating to the base frequency $f_g$ and $f_r$ can be rearranged and expressed as:

$$\frac{U_{ehg}H_{4g}}{U_g} = \left(1 + \frac{Z_{3g}}{Z_{7g}}\right)\cdot\left(\frac{Z_{8g}+Z_{C1g}}{Z_{C1g}}\right)$$

$$= \left[1 + Z_{3g}\left(\frac{1}{Z_{8g}+Z_{C1g}} + \frac{1}{R_g} + \frac{1}{Z_{4g}}\right)\right]\cdot\left(\frac{Z_{8g}+Z_{C1g}}{Z_{C1g}}\right)$$

$$= \left[1 + Z_{3g}\left(\frac{1}{Z_{C1g}} + \frac{1}{R_g} + \frac{1}{Z_{4g}} - \frac{Z_{8g}}{Z_{C1g}(Z_{8g}+Z_{C1g})}\right)\right]\cdot$$

$$\left(\frac{Z_{8g}+Z_{C1g}}{Z_{C1g}}\right)$$

then $$\frac{1}{R_g} + \frac{1}{Z_{C1g}} = \left[\frac{U_{ehg}H_{4g}}{U_g}\cdot\frac{Z_{C1g}}{Z_{C1g}+Z_{8g}} - 1\right]\frac{1}{Z_{3g}} -$$

$$\frac{1}{Z_{4g}} + \frac{Z_{8g}}{Z_{C1g}(Z_{C1g}+Z_{8g})}.$$

Similarly:

$$\frac{U_{ehr}H_{6r}}{U_r} = \left(1 + \frac{Z_{5r}}{Z_{8r}}\right)\cdot\left(\frac{Z_{C1r}+Z_{7r}}{Z_{C1r}}\right)$$

$$= \left[1 + Z_{5r}\left(\frac{1}{Z_{7r}+Z_{C1r}} + \frac{1}{R_r} + \frac{1}{Z_{C2r}} + \frac{1}{Z_{6r}}\right)\right]\cdot\left(\frac{Z_{C1r}+Z_{7r}}{Z_{C1r}}\right)$$

then $$\frac{1}{R_r} + \frac{1}{Z_{C2r}} = \left[\frac{U_{ehr}H_{6r}}{U_r}*\frac{Z_{C1r}}{Z_{C1r}+Z_{7r}} - 1\right]\frac{1}{Z_{5r}} - \frac{1}{Z_{6r}} - \frac{1}{Z_{C1r}+Z_{7r}}$$

If A and B are not equal to 1, the equation shown above will be slightly more complicated, but the basic methodology is the same.

The iteration can comprise the following steps:

First of all, it will be assumed that the resistance $R_r$=0 and the capacitance $C_2$=0 leading to the complex impedance $Z_{8g}$=0, then $$\left(\frac{1}{R_g} + \frac{1}{Z_{C1g}}\right) = \left(\frac{U_{egh}H_{4g}}{U_g} - 1\right)\frac{1}{Z_{3g}} - \frac{1}{Z_{4g}},$$

with $$\frac{1}{R_g}$$

being the real part of the result at the right-hand side of the equation and $$\frac{1}{Z_{C1g}}$$

being the imaginary part.

The second step of the iteration can comprise the assumption that when the resistance $R_g$ is known the complex impedance $Z_{7r}$ is also known and when the complex impedance $Z_{C1g}$ is known, the complex impedance $Z_{C1r}$ is also known:

$$\frac{1}{R_r} + \frac{1}{Z_{C2r}} = \left[\frac{U_{ehr}H_{6r}}{U_r} * \frac{Z_{C1r}}{Z_{C1r}+Z_{7r}} - 1\right]\frac{1}{Z_{5r}} - \frac{1}{Z_{6r}} - \frac{1}{Z_{C1r}+Z_{7r}}$$

with $$\frac{1}{R_r}$$

being the real part of the result at the right-hand side of the equation and $$\frac{1}{Z_{C2r}}$$

being the imaginary part.

The third step of the iteration can comprise the assumption that if the resistance $R_r$ and the complex impedance $Z_{C2g}$ are known, then the complex impedance $Z_{C2g}$ and the complex impedance $Z_{8g}$ are also known. The complex impedance $Z_{C1g}$ on the right side of the equation is known from the previous calculation, then $$\frac{1}{R_g} + \frac{1}{Z_{C1g}} = \left[\frac{U_{ehg}H_{4g}}{U_g} * \frac{Z_{C1g}}{Z_{C1g}+Z_{8g}} - 1\right]\frac{1}{Z_{3g}} - \frac{1}{Z_{4g}} + \frac{Z_{8g}}{Z_{C1g}(Z_{C1g}+Z_{8g})}$$

The real part of the result at the right-hand side of the equation is $$\frac{1}{R_g},$$

and the imaginary part is $$\frac{1}{Z_{C1g}}.$$

The fourth step of the iteration can comprise the determination of the complex impedance $Z_{7r}$ from the new resistance $R_g$, and the determination of the complex impedance $Z_{C1r}$ from the new complex impedance $Z_{C1g}$.

$$\frac{1}{R_r} + \frac{1}{Z_{C2r}} = \left[\frac{U_{ehr}H_{6r}}{U_r} * \frac{Z_{C1r}}{Z_{C1r}+Z_{7r}} - 1\right]\frac{1}{Z_{5r}} - \frac{1}{Z_{6r}} - \frac{1}{Z_{C1r}+Z_{7r}}$$

the real part of the result at the right-hand side of the equation is $$\frac{1}{R_r},$$

while the imaginary part is $$\frac{1}{Z_{C2r}}.$$

The calculated results of the resistances $R_g$, $R_r$ can be accurate enough; otherwise the iteration may be continued.

In step S3a the method for determining the calibration responses $U_{ehg}$ and $U_{ehr}$ by a 4-point-calibration will be described below:

At a first calibration point the resistances are set to $R_r=0$, $R_g=R_{g0}$ and the test response $U_{g0}$ is measured. When the calibration point $Z_{8g}$ is selected as $Z_{8g}=0$ the calculation is considerably simplified and can be expressed as:

$$\frac{1}{R_{g0}} + \frac{1}{Z_{C1g}} = \left(\frac{U_{ehg}H_{4g}}{U_{g0}} - 1\right)\frac{1}{Z_{3g}} - \frac{1}{Z_{4g}}$$

At a second calibration point the resistances are set to $R_r=0$, $R_g=R_{g1}$ and the test response $U_{g1}$ is measured:

$$\frac{1}{R_{g1}} + \frac{1}{Z_{C1g}} = \left(\frac{U_{ehg}H_{4g}}{U_{g1}} - 1\right)\frac{1}{Z_{3g}} - \frac{1}{Z_{4g}}$$

By combining the two equations above with each other the following equation is derived:

$$U_{ehg}H_{4g} = \left(Z_{3g}\left(\frac{1}{R_{g0}} - \frac{1}{R_{g1}}\right)\right) \cdot \left(\frac{1}{U_{g0}} - \frac{1}{U_{g1}}\right)^{-1}$$

The calibration response $U_{ehg}$, or its equivalent such as $U_{ehg}*H_{4g}$, can be stored in the memory for further use. By selecting calibration points in such a way, the resistance $R_r$ and the capacitance $C_2$ will not affect the test response $U_g$, and the calculation during the calibration is simplified considerably.

Similarly, at the third calibration point the resistances are $R_g=0$, $R_r=R_{r0}$ and the test response $U_{r0}$ is determined. At the fourth calibration point the resistances are $R_g=0$, $R_r=R_{r1}$, and the test response $U_{r1}$ is determined.

Again, with these selected calibration points the test response $U_r$ will not be influenced by the resistance $R_g$. With the impedance $Z_{7r}=0$, the calculation is further simplified, which leads to:

$$U_{ehr}H_{6r} = \left(Z_{5r}\left(\frac{1}{R_{r0}} - \frac{1}{R_{r1}}\right)\right) \cdot \left(\frac{1}{U_{r0}} - \frac{1}{U_{r1}}\right)^{-1}$$

The calibration response $U_{ehr}$ or its equivalent parameter such as $U_{ehr}*H_{6r}$ is stored in the memory for further use.

It is also possible to use $(R_g, R_r)=(R_{g0}, R_{r0})$, $(R_{g1}, R_{r0})$, $(R_{g0}, R_{r1})$, $(R_{g1}, R_{r1})$ as a calibration point in order to determine the calibration responses $U_{ehg}$ and $U_{ehr}$. However, the calculation is relatively complicated. Nevertheless the calibration point selection falls within the scope of the present disclosure.

In the steps above, step S3 can, for example, be only utilized for the derivation of expressions comprising the device design and the calibration and step S4 can be a step in the derivation of the expressions. For an actual measurement both steps S3 and S4 can be skipped.

Figure 5:
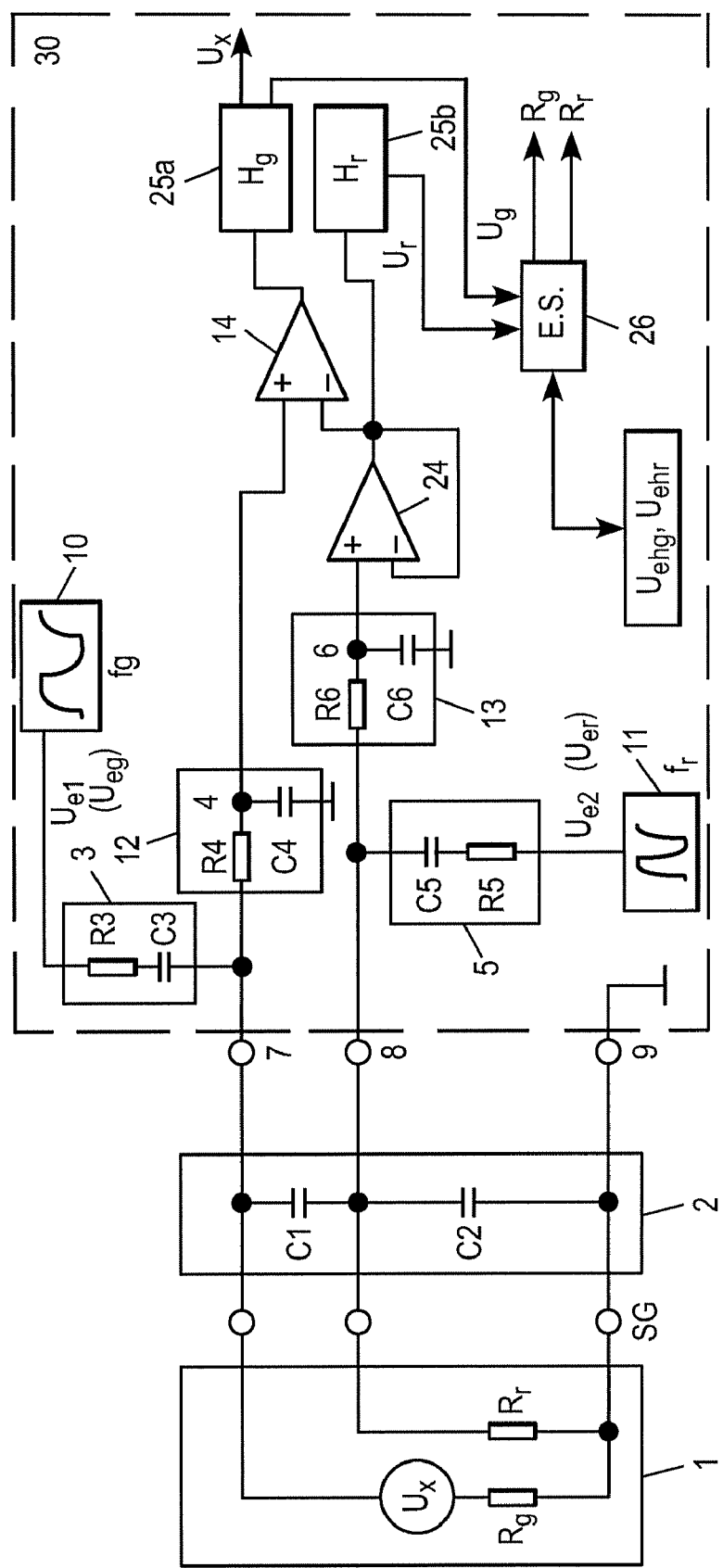
FIG. 5 is an equivalent circuit diagram of an electrode, a connecting cable and a measuring device for an exemplary potentiometric measuring probe according to another embodiment of the disclosure.

FIG. 5 shows an equivalent circuit for the measurement device for a potentiometric measuring probe according to a further embodiment of the present disclosure. In addition to the device presented in FIG. 2, it comprises a voltage follower 24, which output is on one hand sent to the differential amplifier 14, and simultaneously to the A/D converter 25b of the transfer function $H_r$ in order to independently calculate the test response $U_r$, and on the other hand another signal is still sent to the A/D converter 25a of the transfer function $H_g$ through the differential amplifier 14 in order to independently calculate the electrode potential $U_x$ and the test response $U_g$. Compared to FIG. 2 the definition and acquisition of $U_r$ and $U_{ehr}$ are different and the circuit is slightly more complicated, but the influence of $R_g$ on $U_r$ is greatly reduced and it is much easier to obtain an accurate measurement of $R_r$ (especially for large $R_g$). The transfer functions $H_g$ and $H_r$ are separately shown in FIG. 5, but this does not mean that they necessarily must be employed as separate filters and A/D elements. The outputs of the differential amplifier 14 and the voltage follower 24 can be switched to the same A/D converter via multiple path switching means. The A/D converter performs a conversion to the two signals sequentially. The Fourier transformation unit gets sequentially Ux and $U_g$ (the signals from the differential amplifier 14) and $U_r$ (the signal from the voltage follower 24). The circuit can be regarded as stable within a short period of time. In some cases, the two input terminals of the amplifier 14 may each have a voltage follower. In that case, the follower at the negative input terminal serves as the follower 24 and Ur and $U_{ehr}$ are defined as:

$$U_r = U_{6r}H_r = U_{er}\frac{Z_{8r}}{Z_{8r}+Z_{5r}}H_{6r}H_r \text{ and } U_{ehr} = U_{er}^*H_r$$

With $$\frac{U_r}{U_{ehr}} = \frac{Z_{8r}}{Z_{8r}+Z_{5r}}H_{6r}$$

The right to the equal sign gives the second response coefficient.

When solving the equations (the second and fourth steps of step S5 mentioned above), the respective formula for $R_r$ and $C_2$ has to be changed accordingly:

$$\frac{1}{R_r}+\frac{1}{Z_{C2r}}=\left[\frac{U_{ehr}H_{6r}}{U_{6r}}-1\right]\frac{1}{Z_{5r}}-\frac{1}{Z_{6r}}-\frac{1}{Z_{C1r}+Z_{7r}}$$

the other steps are the same as those of the previous embodiment. Therefore, no further detailed description is needed herein.

Some probes do not comprise a solution ground electrode, but the device 30 and 40 can still be utilized. In that case, the connecting points 8 and 9 should be shorted at the device connection terminal and $R_g$ thus measured is actually $R_g+R_r$ and the measured $R_r$ is zero.

Figure 6:
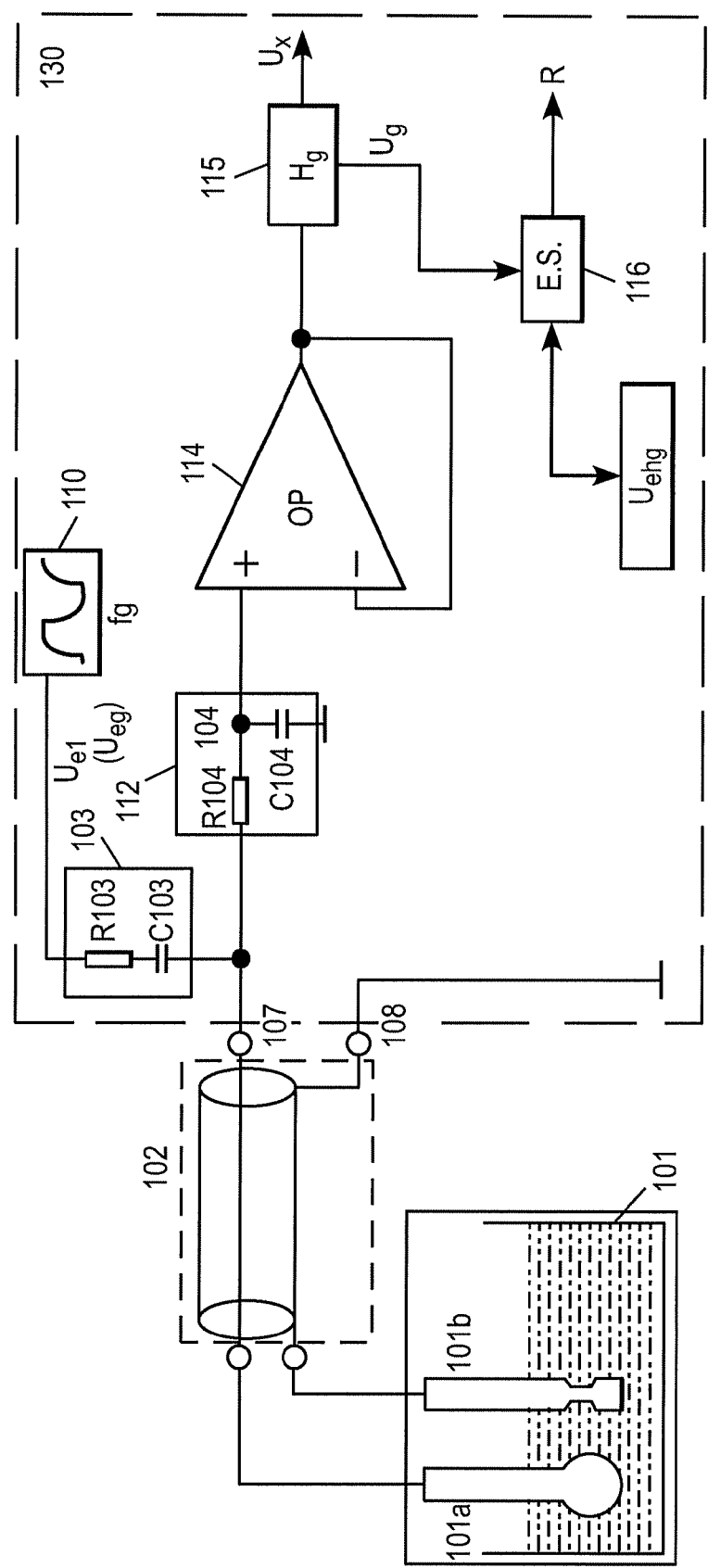
FIG. 6 is a schematic view of an electrode, a connecting cable and an exemplary structure of a measuring device for a potentiometric measuring probe according to another embodiment of the disclosure.

FIG. 6 represents a schematic diagram illustrating another embodiment of the probe, the connecting cable and the potentiometric analysis measurement device. This embodiment is used to measure the internal resistance of the electrode $R=R_g+R_r$. The probe 101 comprises an indicating electrode 101a and a reference electrode 101b, wherein the indicating electrode 101a is connected to the measurement device 130 through the connecting cable 102 while the reference electrode 101b is grounded. The two electrodes have an internal resistance R connected in series, and the electrode 101 and the connecting cable 102 can be represented by their equivalent circuit shown in FIG. 7.

Figure 7:
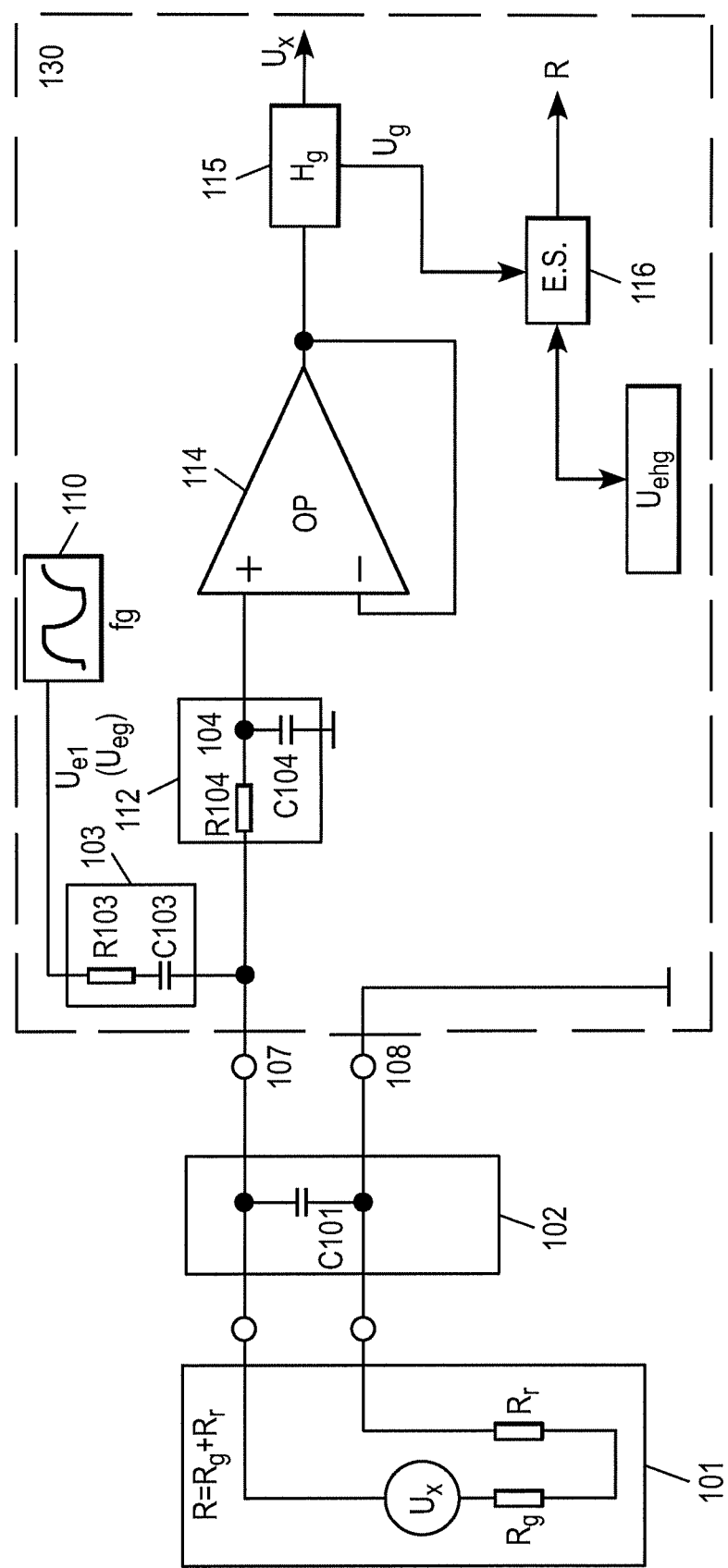
FIG. 7 is an equivalent circuit diagram of FIG. 6.

FIG. 7 shows the equivalent circuit for FIG. 6. As shown in FIG. 7, the probe 101 is represented by a voltage source with an electrode potential $U_x$ and a resistor R, one terminal of the resistor R is grounded. In accordance with the common structure of the connecting cables, the connecting cable 102 is represented by capacitor C101. Capacitor C101 is connected between the connection points 107 and 108. Other connecting cables may have somewhat different equivalent circuits and connections, thus resulting in equations differing from the ones presented below, but the principle and method are the same.

The measurement device comprises a voltage source 110, a voltage source impedance 103, a transfer function unit 115 and a calculation unit 116.

The voltage source 110 generates a test voltage $U_{e1}$, which comprises the harmonic wave $U_{eg}$ with the basic base frequency $f_g$.

The voltage source impedance 103 is connected between the output terminal of the voltage source 110 and the connecting cable 102 for feeding the test voltage $U_{e1}$ into the connecting cable, namely the connection point 107. The voltage source impedance 103 can comprise only capacitance, and in the present embodiment, the voltage source impedance 103 comprises a resistor R103 and a capacitor C103 connected in series.

A filtering unit 112 can be provided following the connection point 107 to reduce electromagnetic interference and electrostatic shock. The filtering unit 112 may comprise an RC low pass filter circuit connected to the non-inverting input terminal of the amplifier 114. In addition to the resistor/capacitor elements, the filtering unit 112 may further comprise inductive devices such as ferrite. However, since the test voltage used to determine the internal resistance R usually has a low base frequency, the inductive devices can be neglected during the R determination. Of course, the method and device of the present disclosure can also be utilized for a setup comprising inductive devices.

The transfer function unit 115 can comprise the gain of an amplifier 114, if applicable a low pass filter, an A/D converter, if applicable a digital filter and a Fourier transformation unit connected in series. These devices are comparable to those shown in FIG. 2, differing in that the amplifier 114 has its non-inverting terminal connected to the connecting cable and its inverting terminal connected to the output terminal so as to form a voltage follower. Alternatively, if the amplifier 114 is of a differential operational amplifier type, its inverting terminal is grounded and its non-inverting terminal is connected to the connecting cable. Similar to FIG. 2, the Fourier transformation unit calculates the potential $U_x$ of the potentiometric measuring probe and the test response $U_g$. For the base frequency signal $f_g$, $H_g$ is the total transfer function of the transfer function unit 115. The test response $U_g$ is the result of the harmonic wave $U_{eg}$ with the base frequency $f_g$ after voltage division by the circuit element(s) preceding the amplifier 114 and passed through the transfer function $H_g$.

The calculation unit 116 is connected to the output terminal of the Fourier transformation unit of the transfer function unit. The internal resistance R of the electrode (1*a*) can be determined by simultaneously solving the equations comprising the unknown parameters, such as the resistance R and the capacitance C101, based on the already known test response $U_g$ as well as the known structure and parameters of the circuit.

The voltage $U_{eg}$ and the transfer function $H_g$ can be determined by establishing a calibration response $U_{ehg} = U_{eg} * H_g$ through a 2-point-calibration. The transfer function $H_g$ is kept the same during the measurement and the calibration, or the difference there between is known. The amplitude, the waveform and the phase of the test voltage $U_{e1}$ are kept the same during the measurement and the calibration, or the differences there between are known. The voltage $U_{eg}$ is kept the same during the measurement and the calibration, or the difference there between is known. In this manner, equations comprising the unknown parameters, the resistance R and the capacitance C101, can be derived from the test response $U_g$ and solving these equations will lead to the internal resistance R.

Figure 8:
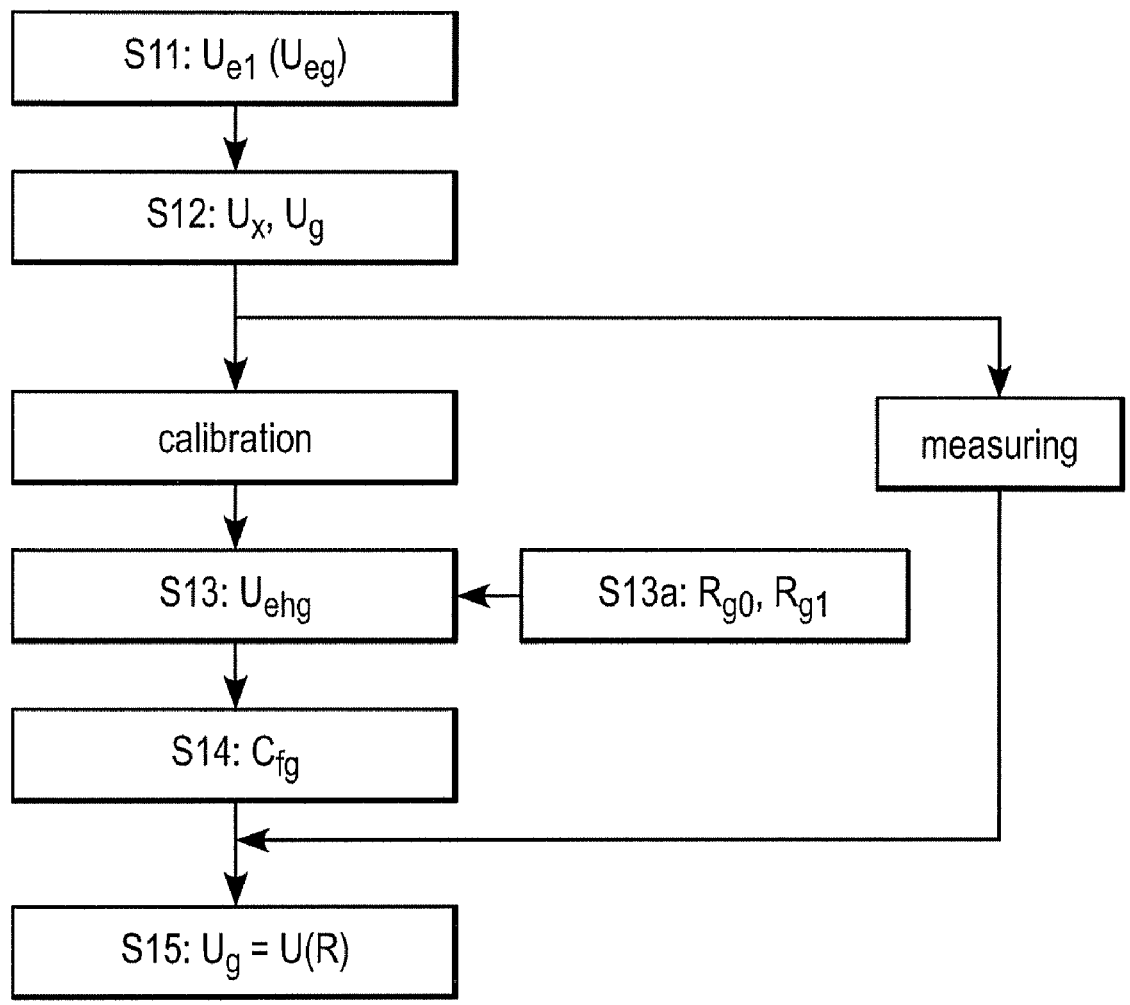
FIG. 8 is an exemplary flowchart of a measuring method for a potentiometric measuring probe according to another embodiment of the disclosure.

Referring to FIG. 8, another embodiment of the measurement method comprises the exemplary steps of:

In step S11 the test voltage $U_{e1}$ is fed to the connecting cable through the voltage source impedance, wherein the test voltage $U_{e1}$ comprises the harmonic wave $U_{eg}$ with the base frequency $f_g$.

In step S12 the voltage of the electrode and the AC response resulting from the test voltage are passed through the operational amplifier, the A/D converter, and the Fourier transformation unit. The potential $U_x$ of the potentiometric measuring probe and the test responses are calculated, respectively. The calculation herein is similar to that of the embodiment shown in FIG. 2, and no detailed description is necessary.

In step S13 a calibration response $U_{ehg}$ is predetermined, wherein the calibration responses $U_{ehg}$ comprises the product of the calibration response $U_{eg}$ with the base frequency $f_g$ and the transfer function $H_g$. The calibration responses $U_{ehg}$ may further comprise other definite product factors. $U_{ehg}$ comprising other definite product factors is considered to be a parameter equivalent to $U_{ehg}$. $H_g$ is the transfer function of a signal with base frequency $f_g$ which is fed into the operational amplifier, passed through A/D converter and outputted from the Fourier transformation unit. The calibration response $U_{ehg}$ can be determined by a 2-point calibration, which will be described in further detail in the following step S13*a*.

In step S14, based on the structural parameters of the circuit, the functional expressions for the test response $U_g$ is established, wherein the test response $U_g$ comprises the product of the calibration response $U_{ehg}$ and a response coefficient defined by the circuit structure and parameters. In more detail this can be expressed as:

$$X_{Ckg} = \frac{1}{2\pi \cdot f_g C_k}, k = 101, 103, 104$$

$$Z_{Ckg} = jX_{Ckg}, k = 101, 103, 104$$

$$Z_{kg} = R_k + Z_{Ckg}, k = 103, 104$$

where the parameters corresponding to k=103, 104 are considered to be known.

$$H_{104g} = \frac{Z_{C104g}}{Z_{104g}}$$

$$Z_{107g} = \left(\frac{1}{Z_{C101g}} + \frac{1}{R} + \frac{1}{Z_{104g}}\right)^{-1}$$

the complex voltage at node 104, relating to base frequency $f_g$ can be derived:

$$U_{104g} = U_{eg} \frac{Z_{107g}}{Z_{107g} + Z_{103g}} \cdot \frac{Z_{C104g}}{Z_{104g}}$$

the relation between the input of operational amplification and the output of Fourier transformation is:

$$U_g = U_{104g} H_g = U_{eg} \frac{Z_{107g}}{Z_{107g} + Z_{103g}} H_{104g} H_g.$$

Let the calibration response be $$U_{ehg} = U_{eg} \cdot H_g.$$

The basic equation relating to base frequency $f_g$ can be derived as:

$$\frac{U_g}{U_{ehg}} = \frac{Z_{107g}}{Z_{107g} + Z_{103g}} H_{104g}$$

The right to the equal sign gives the response coefficient.

In step S15 the known test response $U_g$ and the calibration response $U_{ehg}$ are sent to a calculation unit. The internal resistance R of the electrode is determined by simultaneously solving the equations comprising the unknown resistance R and the capacitance C101 based on the functional expression of the response coefficient, which can be expressed as follows:

$$\frac{U_g}{U_{ehg} H_{104g}} = \frac{Z_{107g}}{Z_{107g} + Z_{103g}} = \frac{1}{1 + \left(\frac{1}{Z_{C101g}} + \frac{1}{R} + \frac{1}{Z_{104g}}\right) Z_{103g}}$$

then $$\frac{1}{R} + \frac{1}{Z_{C101g}} = \left(\frac{U_{ehg} H_{104g}}{U_g} - 1\right) \frac{1}{Z_{103g}} - \frac{1}{Z_{104g}}.$$

The real part of the right-hand side of the equation is 1/R while the imaginary part is $$\frac{1}{Z_{C101g}}.$$

In step S13*a* the 2-point-calibration determination of the calibration response $U_{ehg}$ is described as follows:

At the first calibration point the resistance $R=R_0$ and the test response $U_{g0}$ are determined;

at the second calibration point the resistance $R=R_1$ and the test response $U_{g1}$ are determined.

In a similar way to the step S3a described above, it can be derived:

$$U_{ehg}H_{104g} = \left(Z_{103g}\left(\frac{1}{R_0} - \frac{1}{R_1}\right)\right) \cdot \left(\frac{1}{U_{g0}} - \frac{1}{U_{g1}}\right)^{-1}$$

The calibration response $U_{ehg}$ or its equivalent parameter, such as $U_{ehg}H_{104g}$ is stored in the memory for further use.

In an exemplary embodiment, resistors and capacities are chosen to be: C3=100 pF, C4=100 pF, C5=1 uF, C6=100 pF, Fg=6 Hz, Fr=12 Hz, R3=470 kΩ, R4=100 kΩ, R5=470 kΩ, R6=100 kΩ.

The embodiments described above are preferred exemplary embodiments of the present disclosure. Various equivalent substitutions and modifications can be made by one skilled in the art based on the foregoing description of the embodiments of the disclosure. Nevertheless, all these substitutions and modifications made based on the embodiments of the disclosure fall within the spirit and scope of the present disclosure as defined in the appended claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCES 1, 101 potentiometric measuring probe
1a, 101a indicating electrode
1b, 101b reference electrode
2, 102 connecting cable
2, 2a, 2b, 102a, 102b core
3, 5 103, 105 voltage source impedance
4, 6, 7, 8, 107, 108 connecting point
10, 11, 110 voltage source
12, 13 filtering unit
14, 114 amplifier
15, 115 transfer function unit
15a operational amplifier
15b, 15d low pass filter
15c A/D converter
15e Fourier transformation unit
16, 116 calculation unit
30, 130 measuring device
fg, $f_r$ base frequency
$U_{e1}$, $U_{e2}$ test voltage
SG solution grounding electrode
$R_g$, $R_r$ electrode resistors
$R_{g0}$, $R_{g1}$, $R_{r0}$, $R_{r1}$ calibration resistances
$U_x$ electrode potential difference
$C_{fg}$, $C_{fr}$ response coefficient
$U_g$, $U_r$ test response
$U_{ehg}$, $U_{ehr}$ calibration response
$C_1$, $C_2$, $C_3$, $C_4$, $C_5$, $C_6$, $C_7$ capacitor
$U_{e1}$, $U_{e2}$ alternating test voltage
$U_{eg}$, $U_{er}$ sine voltage
$H_g$, $H_r$ signal transfer function
V responding electrode voltage
X(i) A/D output
R1, R2, R3, R4, R5, R6 resistor

What is claimed is:

1. Method for observing the condition of a measuring device having a potentiometric measuring probe which comprises at least two electrodes, each having a resistance, the method comprising:

applying an alternating test voltage provided by a voltage source via a connecting cable to at least one of the electrodes;

passing a combined signal containing a potentiometric voltage of the electrode and a signal that relates to the applied alternating test voltage to a processing unit;

extracting from the combined signal the signal that relates to the applied alternating test voltage in the processing unit; and calculating from the signal that relates to the applied alternating test voltage a resistance of the at least one electrode, wherein the combined signal is processed in the processing unit by a transfer function unit, which substantially simultaneously extracts from the combined signal a measurement value which corresponds to the potentiometric signal of the at least one electrode and a test response that is used for calculating the resistance of the at least one electrode, and wherein the alternating test voltage comprises a sine shaped signal component with a base frequency at least during a calibration time period.

2. Method according to claim 1, wherein the alternating test voltage is, where appropriate after subtraction of a constant voltage component, substantially symmetrical in relation to negative and positive voltage values.

3. Method according to claim 1, comprising:
applying at least two alternating test voltages, each having at least one signal component corresponding to the base frequency, and wherein the alternating test voltages are disjunctive.

4. Method according to claim 1, comprising:
applying two alternating test voltages, which differ by a ratio of their base frequencies according to an expression: $f_g = m^* f_r$ or $f_r = m^* f_g$, wherein $f_g$ is a first base frequency, $f_r$ is a second base frequency, and m is an even number larger than or equal to 2.

5. Method according to claim 4, wherein a first alternating test voltage is applied to a first of the two electrodes and a second alternating test voltage is applied to a second of the two electrodes.

6. Method according to claim 5, wherein the combined signal is processed in the transfer function unit by calculating at least one frequency component of a Fourier Transformation, wherein the test response is extracted corresponding to the base frequency and/or to at least one frequency component of the alternating test voltage.

7. Method according to claim 6, wherein the combined signal is processed by an analog-digital conversion and passed, where appropriate after digital low pass filtering, to a Fourier transformation unit or to a calculation unit.

8. Method according to claim 7, wherein the combined signal is preprocessed and/or amplified and/or converted by one or multiple amplifiers and passed, via a low pass filter, to an input of an A/D converter or to a Fourier transformation unit or to a calculation unit.

9. Method according to claim 8, comprising:
a calibration process for determining at least one calibration response by applying an alternating sine voltage to the at least one electrode.

10. Method according to claim 9, wherein during the calibration process at least one response coefficient is calculated from an impedance equation, which comprises at least one impedance of the measuring device.

11. Method according to claim 10, wherein the resistance of the at least one electrode is determined by solving an impedance equation, which corresponds to the measuring device and which relates the test response to the resistance of the at least one electrode.

12. Method according to claim 11, wherein the impedance equation of the measuring device comprises the impedance of the at least one electrode and/or the impedance of the connecting cable and/or the impedance of the processing unit and/or a DC-blocking/current-limiting impedance of the voltage source and/or an impedance of a filtering unit that filters the combined signal received at an input of the processing unit.

13. Method according to claim 12, wherein the impedance equation is solved by including at least one, previously determined, intermediate value, which is given by at least one calibration response and/or by at least one response coefficient.

14. Method according to claim 1, wherein a first alternating test voltage is applied to a first of the two electrodes and a second alternating test voltage is applied to a second of the two electrodes.

15. Method according to claim 1, wherein the combined signal is processed in the transfer function unit by calculating at least one frequency component of a Fourier Transformation, wherein the test response is extracted corresponding to the base frequency and/or to at least one frequency component of the alternating test voltage.

16. Method according to claim 1, wherein the combined signal is processed by an analog-digital conversion and passed, where appropriate after digital low pass filtering, to a Fourier transformation unit or to a calculation unit.

17. Method according to claim 1, wherein the combined signal is preprocessed and/or amplified and/or converted by one or multiple amplifiers and passed, via a low pass filter, to an input of an A/D converter or to a Fourier transformation unit or to a calculation unit.

18. Method according to claim 1, comprising:
a calibration process for determining at least one calibration response by applying an alternating sine voltage to the at least one electrode.

19. Method according to claim 18, wherein during a calibration process the at least one calibration response is determined by replacing the resistance of the at least one electrode by a calibration resistance.

20. Method according claim 19, wherein the calibration response is determined by a 4-point-calibration process, which is conduced by selecting four different settings of a pair of calibration resistances, a first value of the pair representing the resistance of the first electrode and a second value representing the resistance of the second electrode, or by a 2-point-calibration process by selecting two different calibration resistances for the first electrode.

21. Method according claim 20, wherein for the four-point-calibration process, the four calibration points are chosen to be: $(R_{g0}, 0), (R_{g1}, 0), (0, R_{r0})$ and $(0, R_{r1})$, with $R_{g0}$ and $R_{g1}$ as well as $R_{r0}$ and $R_{r1}$ being different calibration resistances.

22. Method according to claim 18, wherein during the calibration process at least one response coefficient is calculated from an impedance equation, which comprises at least one impedance of the measuring device.

23. Method according to claim 22, wherein the impedance equation of the measuring device comprises the impedance of the at least one electrode and/or the impedance of the connecting cable and/or the impedance of the processing unit and/or a DC-blocking/current-limiting impedance of the voltage source and/or an impedance of a filtering unit that filters the combined signal received at an input of the processing unit.

24. Method according to claim 22, wherein impedance equation is solved by including at least one intermediate value, which is given by at least one calibration response and/or by at least one response coefficient.

25. Method according to claim 1, wherein the resistance of the at least one electrode is determined by solving an impedance equation, which corresponds to the measuring device and which relates the test response to the resistance of the at least one electrode.

26. Method according to claim 25, wherein a first impedance equation for a first test response and a second impedance equation for a second test response are solved simultaneously to determine a first resistance of a first of the two electrodes and a second resistance of a second of the two electrodes.

27. Method according to claim 1, wherein the alternating test voltage comprises at least one further sine shaped, harmonic signal component corresponding to the base frequency during at least a test time period in which the alternating test voltage is applied to the at least one electrode.

28. Method according to claim 27, comprising:
applying two alternating test voltages, which differ by a ratio of their base frequencies according to an expression: $f_g=m*f_r$ or $f_r=m*f_g$, wherein $f_g$ is a first base frequency, $f_r$ is a second base frequency, and m is an even number larger than or equal to 2.

29. Device for observing the condition of a potentiometric measuring probe having at least two electrodes, each having an electrical resistance, at least one electrode being connected via a connecting cable to a voltage source configured for providing an alternating test voltage, the device comprising:
a processing unit with an input configured to be connected to the connecting cable, and configured to receive a combined signal containing a potentiometric voltage of the at least one electrode and a signal that relates to the applied alternating test voltage and to extract from the combined signal a signal which corresponds to a signal that results from the applied alternating test voltage, wherein the processing unit comprises a transfer function unit configured to substantially simultaneously extract from the combined signal a measurement value which corresponds to the potentiometric voltage of the at least one electrode which is provided at a first output, and a test response which is provided via a second output to a calculation unit
wherein the alternating test voltage comprises a sine shaped signal component with a base frequency at least during a calibration time period.

30. Device according to claim 29, wherein the transfer function unit is embodied as a Fourier transformation unit, which extracts the test response corresponding to at least one base frequency component of the alternating test voltage.

31. Device according to claim 30, wherein the transfer function unit comprises an A/D converter that receives the combined signal and that is connected with its output, where appropriate via a digital low pass filter, to the input of a Fourier transformation unit or to a calculation unit.

32. Device according to claim 31, wherein the transfer function unit comprises one or multiple operational amplifiers that receive the combined signal, an output of the operational amplifiers being connected via a low pass filter, to an input of an A/D converter or to a Fourier transformation unit or to a calculation unit.

33. Device according to claim 32, wherein the transfer function unit is configured for connection to the at least one electrode via the connecting cable and via an amplifier.

34. Device according to claim 33, comprising, in combination, a first electrode connected to a first input of the amplifier and a second electrode connected to a second input of the amplifier, the amplifier being configured to output a combined signal which corresponds to a difference of the combined signal of the first electrode and a combined signal of the second electrode.

35. Device according to claim 34, wherein the voltage source comprises:
- a DC-blocking and/or current-limiting impedance, which includes a capacitor and/or a resistor and the voltage source is configured for connection to the at least one electrode via the DC-blocking and/or current-limiting impedance.

36. Device according to claim 35, comprising:
- a filtering unit, which is a RC low pass filter circuit having a capacitor and a resistor, the filtering unit being connected to the transfer function unit or to an amplifier, and being configured to receive an input from the at least one electrode.

37. Device according to claim 29, wherein the transfer function unit comprises an A/D converter that receives the combined signal and that is connected with its output, where appropriate via a digital low pass filter, to the input of a Fourier transformation unit or to a calculation unit.

38. Device according to claim 29, wherein the transfer function unit comprises one or multiple operational amplifiers that receive the combined signal, an output of the operational amplifiers being connected to a low pass filter, to an input of an A/D converter, to a Fourier transformation unit or to a calculation unit.

39. Device according to claim 29, wherein the transfer function unit is configured for connection to the at least one electrode via the connecting cable and via an amplifier.

40. Device according to claim 39, comprising, in combination, a first electrode connected to a first input of the amplifier and a second electrode connected to a second input of the amplifier, the amplifier being configured to output a combined signal which corresponds to a difference of the combined signal of the first electrode and a combined signal of the second electrode.

41. Device according to claim 29, wherein the voltage source comprises:
- a DC-blocking and/or current-limiting impedance, wherein the voltage source is configured for connection to the at least one electrode via the DC-blocking and/or current-limiting impedance.

42. Device according to claim 29, comprising:
- a filtering unit, which is a low pass filter circuit, the filtering unit being connected to the transfer function unit or to an amplifier, and being configured to receive an input from the at least one electrode.

* * * * *